US010737026B2

(12) United States Patent
Teutsch

(10) Patent No.: US 10,737,026 B2
(45) Date of Patent: Aug. 11, 2020

(54) TRANSFILLING DEVICE

(71) Applicant: Roche Diabetes Care, Inc., Indianapolis, IN (US)

(72) Inventor: David Teutsch, Aarberg (CH)

(73) Assignee: Roche Diabetes Care, Inc., Indianapolis, IN (US)

( * ) Notice: Subject to any disclaimer, the term of this patent is extended or adjusted under 35 U.S.C. 154(b) by 25 days.

(21) Appl. No.: 15/772,171

(22) PCT Filed: Nov. 8, 2016

(86) PCT No.: PCT/EP2016/076922
§ 371 (c)(1),
(2) Date: Apr. 30, 2018

(87) PCT Pub. No.: WO2017/080974
PCT Pub. Date: May 18, 2017

(65) Prior Publication Data
US 2018/0311436 A1    Nov. 1, 2018

(30) Foreign Application Priority Data

Nov. 11, 2015 (EP) .................................... 15194021

(51) Int. Cl.
*A61M 5/178* (2006.01)
*B65B 3/00* (2006.01)
(Continued)

(52) U.S. Cl.
CPC ....... *A61M 5/1782* (2013.01); *A61M 5/14244* (2013.01); *A61M 2005/2414* (2013.01); *A61M 2209/045* (2013.01)

(58) Field of Classification Search
CPC ........ A61M 5/1752; A61M 2005/2414; A61M 5/14244; A61M 2209/045; A61M 2005/14268; B65B 3/003
(Continued)

(56) References Cited

U.S. PATENT DOCUMENTS 5,858,001 A * 1/1999 Tsals ................. A61M 5/14248
604/135
8,720,496 B2 * 5/2014 Huwiler ............ A61M 5/14244
141/10
(Continued)

FOREIGN PATENT DOCUMENTS

CA    2 820 070       8/2012
JP    2014-506497 A   3/2014
(Continued)

OTHER PUBLICATIONS

International Patent Application PCT/EP2016/076922 International Search Report dated Mar. 8, 2017. 2 pages.

*Primary Examiner* — Jessica Cahill
*Assistant Examiner* — Stephanie A Shrieves
(74) *Attorney, Agent, or Firm* — Woodard, Emhardt, Henry, Reeves & Wagner, LLP

(57) ABSTRACT

Disclosed is a transfilling device (1) for transfilling a liquid drug from a cartridge (3) to a flexible reservoir (4). The transfilling device (1) includes a support unit (111) and a plunger (113), the support unit (111) configured to receive the cartridge (3), the plunger (113) being insertable into the cartridge (3), wherein the plunger (113) is displaceable relative to the support unit (111) along an advancement direction (2) between a plunger retracted position, where the plunger (113) is in a most distal position relative to the support unit (111), and a plunger advanced position, where the plunger (113) is in a most proximal position relative to the support unit (111), wherein the plunger (113) is config-
(Continued)

Figure 1:
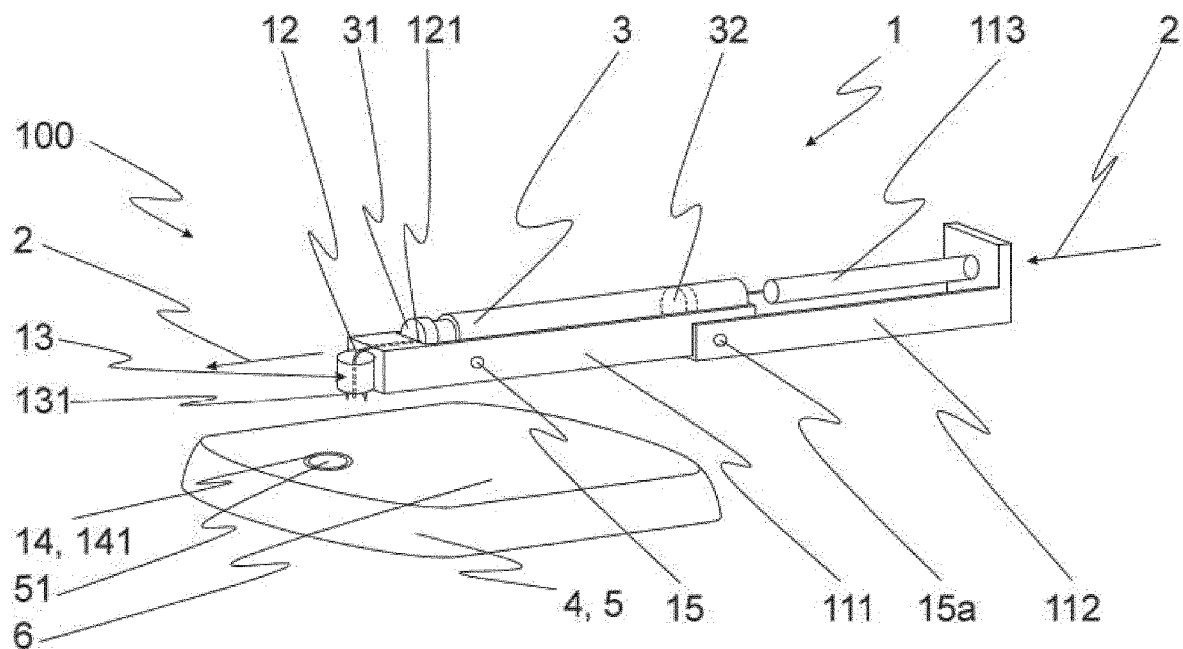

ured to push a piston (32) of the cartridge (3) from a piston retracted position to a piston advanced position by displacing the plunger (113). The transfilling device (1) further includes a transfer cannula (12, 12'), wherein the transfer cannula (12, 12') is configured to penetrate a flexible reservoir septum (41) with a cannula outlet end (122) and to penetrate a cartridge septum (31) with a cannula inlet end (121) and thereby to fluidly couple the flexible reservoir (4) with the cartridge (3). The transfilling device further includes a reservoir locking unit (13), wherein the reservoir locking unit ( ) is configured to releasably mechanically couple the support unit (111) to the flexible reservoir (4) and wherein the coupling of the reservoir locking unit (13) is designed such that the coupling is released in the plunger advanced position.

26 Claims, 4 Drawing Sheets

(51) Int. Cl.
*A61M 5/142* (2006.01)
*A61M 5/24* (2006.01)

(58) Field of Classification Search
USPC .......................................................... 141/114
See application file for complete search history.

(56) References Cited

U.S. PATENT DOCUMENTS

| | | | |
|---|---|---|---|
| 2008/0051765 A1* | 2/2008 | Mounce | A61J 1/1406 604/890.1 |
| 2008/0154205 A1* | 6/2008 | Wojcik | A61M 5/158 604/164.01 |
| 2008/0215030 A1* | 9/2008 | Ritsher | A61J 1/062 604/413 |
| 2011/0218497 A1* | 9/2011 | Assaf | A61M 5/20 604/173 |
| 2012/0078222 A1* | 3/2012 | Smith | A61M 5/16877 604/506 |
| 2013/0102965 A1* | 4/2013 | Teutsch | A61M 5/158 604/164.04 |
| 2013/0253430 A1* | 9/2013 | Kouyoumjian | A61M 5/1408 604/151 |
| 2014/0083517 A1* | 3/2014 | Moia | A61M 39/10 137/15.01 |
| 2015/0126934 A1* | 5/2015 | Chong | A61M 5/158 604/164.11 |

FOREIGN PATENT DOCUMENTS

| | | | | |
|---|---|---|---|---|
| WO | WO 2001/052990 A1 | 7/2001 | | |
| WO | WO 2010/044064 A1 | 4/2010 | | |
| WO | 2012/103428 A2 | 8/2012 | | |
| WO | WO 2014/154777 A1 | 10/2014 | | |
| WO | WO-2014154777 A1 * | 10/2014 | | A61M 5/1782 |

* cited by examiner

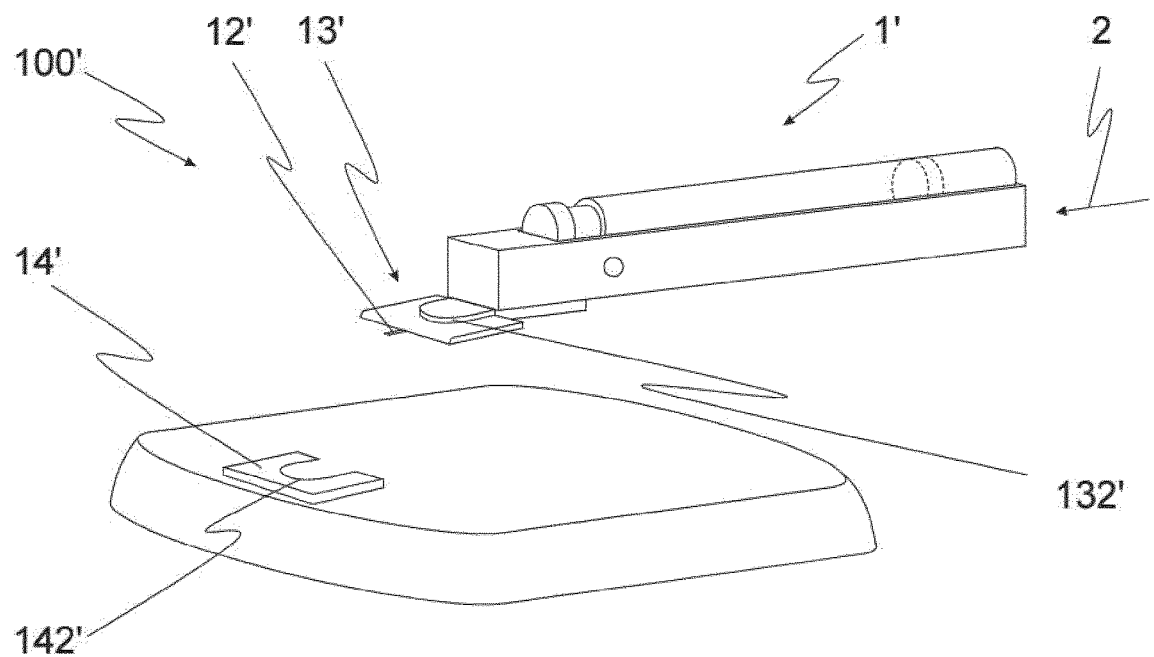
Fig. 3
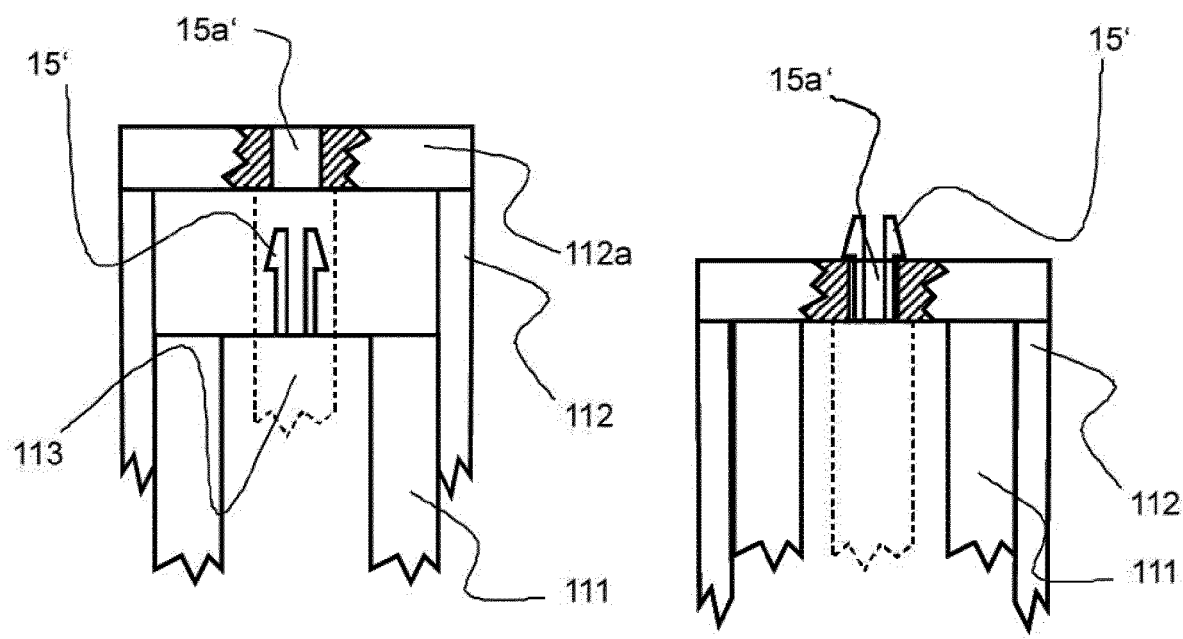
Fig. 4a  Fig. 4b

TRANSFILLING DEVICE

TECHNICAL FIELD

The present invention relates to devices and methods for transfilling liquid drugs between cartridges, ampoules, containers and reservoirs and to assemblies including such devices.

BACKGROUND

The need for transfilling liquid drugs exists in various medical fields. Particularly, a considerable and increasing number of persons with diabetes (PwD) rely on Continuous Subcutaneous Insulin Infusion (CSII) via miniaturized and computer-controlled infusion pumps to supply insulin to the body in a continuous way night and day. In classic systems of this type, a generally cylindrical insulin glass or plastic cartridge is emptied by displacing a piston via a plunger rod in a controlled way (syringe-driver pump). In recent times, however, a number of alternative approaches have and are being proposed and developed which use flexible or semi-flexible insulin reservoirs, such as bags or pouches rather than rigid containers. Examples for such flexible or semi-flexible containers are disclosed, for example, in EP2179755 B1. Typical filling volumes for such insulin reservoirs lay in a range of, for example, 1 ml to 4 ml. This amount of insulin is sufficient for a number of days of therapy for most PwDs. Mainly for safety and regulatory reasons, the reservoirs are generally one-way products that are discarded and replaced after a single use.

SUMMARY OF THE DISCLOSURE

For various reasons, the insulin reservoirs, and particularly flexible insulin reservoirs, are not available filled with insulin and in a state ready for use, but need to be filled from a primary reservoir by the PwD or another person relative immediately prior to their use.

In many cases, the primary reservoir is a so-called "pen cartridge", that is, a rigid cylindrical (glass) cartridge of the above-described general design as used in large numbers in pen-shaped insulin injection devices for manual insulin injection (so-called "insulin pens"). The process of filling a destination reservoir from a primary reservoir, and in particular the process of filling a flexible or semi-flexible reservoir from a rigid cartridge is in this document generally referred to as "transfilling".

Since the largely available pen cartridges are originally designed for the different type of application, their filling volume does typically not match with the filling volume of the flexible reservoir. As explained before, the task of filling a reservoir typically occurs every few days.

In this context, it further has to be considered that PwDs relying on CSII include elderly people and/or people that are visually and/or motoric impaired.

The simplest and most straight-forward approach is the filling of the reservoir via a simple syringe. This procedure, however, is very inconvenient and cannot be properly handled by many users on a regular basis. Further existing transfilling devices for this purpose are bulky, complicated in use, and/or costly.

It is an overall object of the present invention to improve the state of the art of transfilling of liquid drugs from a cartridge to a reservoir. Favourably, the before-mentioned and/or further drawbacks of the prior art are avoided at least in part.

This overall object is achieved by the subject matter of the independent claims. Exemplary and/or particularly favourable embodiments are further defined by the dependent claims and the overall disclosure of this document.

According to one aspect, the overall object is achieved by a transfilling device for transfilling a liquid drug from a cartridge to a flexible reservoir. The transfilling device includes a support unit and a plunger. The support unit may be configured to receive the cartridge. The plunger may be insertable into the cartridge. The plunger may particularly be insertable into the cartridge and in particular into a (typically cylindrical) cartridge body from an open (distal) end. The plunger is displaceable relative to the support unit along an advancement direction between a plunger retracted position, where the plunger is in a most distal position relative to the support unit, and a plunger advanced position, where the plunger is in a most proximal position relative to the support unit. The plunger is configured to push a piston of the cartridge from a piston retracted position where the piston is positioned in a rear area of the cartridge body to a piston advanced position by displacing the plunger.

The liquid drug inside the cartridge is pushed out of the cartridge by the displacement of the piston from the piston retracted position to the piston advanced position. The liquid drug may be insulin or another liquid drug formulation.

The transfilling device may further include a transfer cannula, wherein the transfer cannula is configured to penetrate a flexible reservoir septum with a cannula outlet end and to penetrate a cartridge septum with a cannula inlet end and thereby to fluidly couple the flexible reservoir with the cartridge. The cartridge septum and the flexible reservoir septum, respectively, generally close and seal fluidic openings of the cartridge and the flexible reservoir, respectively, in a tight way, but enable establishing a temporary fluidic connection by piercing the septa with a cannula as described before. Typical septa are self-sealing if the cannula is removed.

The transfer cannula may be maintained by the support unit. In particular, the transfer cannula may be, at least in part, arranged inside the support unit. In embodiments with a reservoir locking unit as discussed further below, the transfer cannula may be, at least in part, arranged inside the reservoir locking unit. Typically, the transfer cannula is unreleasably mounted into the support unit, for example by gluing, welding, during an injection moulding process, or the like.

In typical embodiments, the transfilling device is designed as a disposable device that is discarded after a single application. Therefore, the transfilling device is favourably made of a low number of low-cost components. Alternatively, however, the transfilling device may be partly or fully reusable.

Optionally, the transfilling device may further include a reservoir locking unit, wherein the reservoir locking unit is configured to releasable mechanically couple the support unit to the flexible reservoir and wherein the coupling of the locking unit is designed such that the coupling is released in the plunger advanced position. The advantage of such a reservoir locking unit is that the transfilling device can be automatically released from the flexible reservoir as soon as the transfilling of the drug is completed and thus the user does not have to manually remove the transfilling device from the flexible reservoir after completing the transfilling. The reservoir locking unit may include locking elements such as latches, pins and/or catches that are designed to interact with corresponding counter reservoir-locking elements of the flexible reservoir and/or clothing in which the flexible reservoir is contained.

In some embodiments, the support unit may be designed to receive a cylindrical cartridge having a filling volume between 1 ml and 4 ml. This is a typical filling volume range for cartridges that are generally designed for use in an injection pen as explained above. Some frequently used pen cartridges, for example, have a filling volume of 3 ml. Alternatively, however, the support unit may be designed to receive cartridges of other filling volume and/or design, including non-cylindrical cartridges.

In some embodiments, the plunger and the support unit may be configured to unreleasably lock in the plunger advanced position. The unreleasable locking of the support unit and the plunger in the plunger advanced position prevents the reuse of the transfilling device after completing the transfilling of the liquid drug to the flexible reservoir. This is generally favourable with respect to safety and sterility. For the locking, the transfilling device may include a plunger locking unit with locking elements such as latches, catches, pins, notches, or the like. The plunger, when being locked in the plunger advanced position, is inserted into the cartridge as explained before. Consequently, the cartridge can not be removed from the transfilling device but is discarded together with the transfilling device after use, which is favourable for safety reasons. Any excess insulin that may still be present in the cartridge, is also discarded for this type of embodiment.

In some embodiments, the plunger may include a motor coupler, configured to couple to a motor. The motor may be used to automatically transfill the liquid drug from the cartridge to the flexible reservoir via a motorized advancement of the plunger.

In some embodiments with a motor coupler, the plunger may be part of the motor coupler, directly pushing the piston of the cartridge.

In some embodiments, the plunger may be manually movable by a handling element attached to or formed integral with the plunger, the handling element for example being a handle or grip. A transfilling device with manually movable plunger has the advantage of being cheap in manufacture and simple in composition.

In some embodiments, the plunger may be movable both manually and by a motor. This has for example the advantage that the transfilling device can be used even if the motor is broken by moving the plunger manually.

In some embodiments, the transfilling device may further include a sliding unit, wherein the plunger is formed integral with the sliding unit, the sliding unit being configured for sliding engagement with the support unit. The sliding unit may for example provide an increased stability of the transfilling device and prevent displacement of the plunger in other directions than in the advancement direction. For this type of embodiment, movement of the plunger relative to the support unit is limited to a linear displacement movement between the plunger retracted position and the plunger advanced position, respectively.

According to a further aspect, the overall object is achieved by a reservoir assembly including a flexible reservoir and a transfilling device as disclosed in this document. The flexible reservoir may especially be a flexible reservoir as generally described above and used in combination with insulin pumps and/or similar applications. The flexible reservoir may either be fully flexible and made of, for example, two sheets of a membrane- or foil-like material that are sealing and fluid-tight connected at the edges. Alternatively, the flexible reservoir may be semi-rigid and may be made of a generally rigid shell element and a flexible cover element in form of a foil, membrane, or the like. Typically, the flexible reservoir further includes a filling port that is covered and sealed by a reservoir septum.

In some embodiments of the reservoir assembly, the reservoir assembly may further include a rigid housing, wherein the flexible reservoir is mounted inside the rigid housing and the rigid housing includes a port. The rigid housing may preferably be made of plastic. Alternatively, the rigid housing may be made of any other rigid material. The rigid housing may provide an increased stability of the reservoir assembly and protect the flexible reservoir from damage.

In some embodiments of the reservoir assembly, the reservoir assembly may further include a counter reservoir-locking unit, the counter reservoir-locking unit configured to engage with the reservoir locking unit.

In some embodiments of the reservoir assembly, the rigid housing may include the counter reservoir-locking unit, the counter reservoir-locking unit being configured to engage with the reservoir locking unit. The reservoir locking unit may indirectly couple the support unit to the flexible reservoir, the coupling being mediated through the rigid housing. Embodiments including the counter reservoir-locking unit in the rigid housing may have the advantage of increased stability of the coupling between the support unit and the flexible reservoir.

In some embodiments of the reservoir assembly, the flexible reservoir may have a main extension plane, the main extension plane being substantially parallel to the advancement direction. In further embodiments, the main extension plane of the flexible reservoir may be substantially perpendicular to the advancement direction. In further embodiments, the main extension plane of the flexible reservoir may have any other orientation with respect to the advancement direction. The main extension plane of the rigid housing may coincide with the main extension plane of the flexible reservoir. Such arrangement can be designed to be particularly slim.

According to a further aspect, the object is achieved by an infusion system including a dosing unit and the reservoir assembly as disclosed in this document, wherein the reservoir assembly is fluidly coupled to the dosing unit.

EXEMPLARY EMBODIMENTS

In the following, exemplary embodiments are discussed in more detail with additional reference to the figures.

FIG. 1 shows a simplified perspective view of an embodiment of a reservoir assembly.

FIG. 2*a-d* show simplified side views of the different configurations of the reservoir assembly as shown in FIG. 1 during transfilling.

FIG. 3 shows another embodiment of a reservoir assembly.

FIG. 4*a*, 4*b* show an embodiment of a plunger locking unit.

Figure 5A:
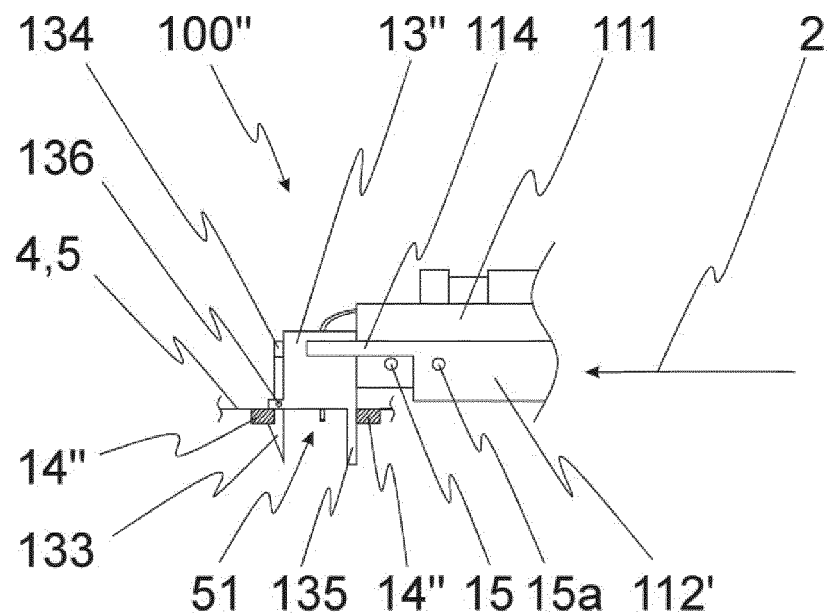
Figure 5B:
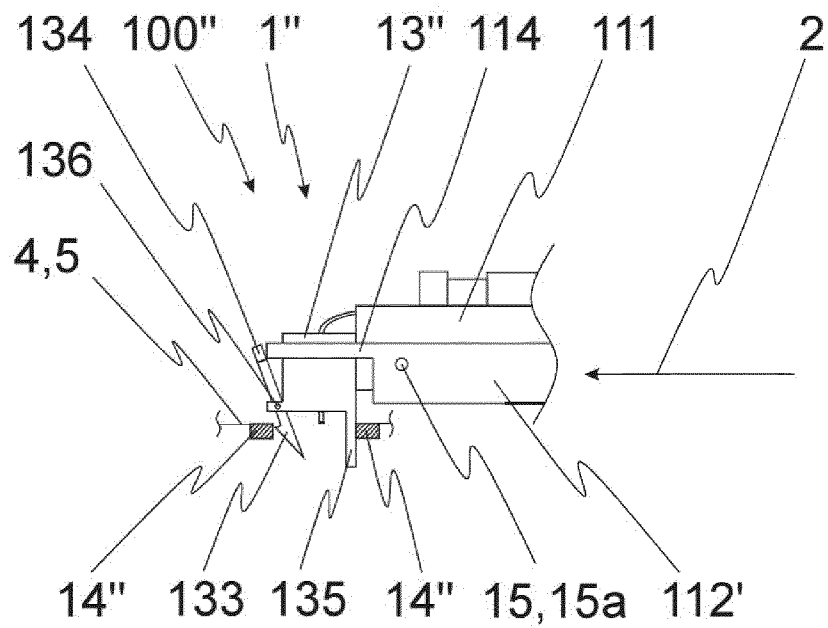

FIG. 5*a*, 5*b* show a further embodiment of a reservoir assembly.

FIG. 1 shows a perspective view of a reservoir assembly 100 including a rigid housing 5 and a transfilling device 1. The rigid housing 5 includes a port 51. A flexible reservoir 4 (not visible) is mounted inside the rigid housing 5. The transfilling device 1 includes a support unit 111, a sliding unit 112, the sliding unit 112 being formed integral with a plunger 113, and a reservoir locking unit 13. A plunger locking unit is shown comprising pins 15 arranged at the support unit 111, and notches 15a arranged at the sliding unit 112. The pins 15 and the notches 15a are configured such that they may unreleasably engage when the plunger 113 is in the plunger advanced position as explained in more detail further below. A cartridge 3 is received by the support unit 111. The cartridge 3 includes a piston 32 in a piston retracted position. The plunger 113 is shown in a plunger retracted position, where the plunger 113 is in a most distal position relative to the support unit 111. For better understanding, the flexible reservoir 4 and the support unit 111 are shown in an uncoupled configuration. The main extension plane 6 of the rigid housing 5 is substantially parallel to the advancement direction 2. In other embodiments, the main extension plane 6 of the rigid housing 5 may be perpendicular, or, in any other direction with respect to the advancement direction 2. The rigid housing 5 includes a port 51 and a counter reservoir-locking unit 14. The counter reservoir-locking unit 14 is configured to releasable couple to the reservoir locking unit 13. In the shown embodiment, the reservoir locking unit 13 comprises clips 131 mating with corresponding slots 141 of the counter reservoir-locking unit 14. A transfer cannula 12 is shown penetrating a cartridge septum 31 with a cannula inlet end 121. The transfer cannula 12 is partially arranged inside the support unit 111 and partially inside the reservoir locking unit 13. The parts of the transfer cannula 12 arranged inside the support unit 111 and the reservoir locking unit 13 are indicated using dashed lines.

FIG. 2a-d show side views of the different configurations of the reservoir assembly 100 during transfilling.

Figure 2A:
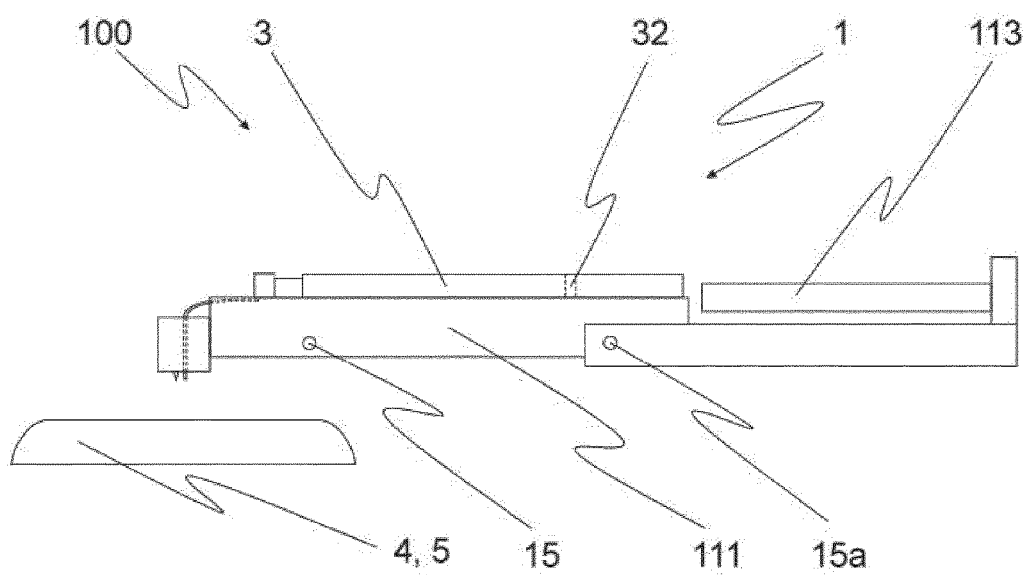

FIG. 2a shows the reservoir assembly 100 according to FIG. 1 before transfilling, where the transfilling device 1 and the rigid housing 5 including the flexible reservoir 4 (not visible) are not coupled. The plunger 113 is in the plunger retracted position. The support unit 111 receives a cartridge 3 where the piston 32 of the cartridge 3 is in a piston retracted position.

Figure 2B:
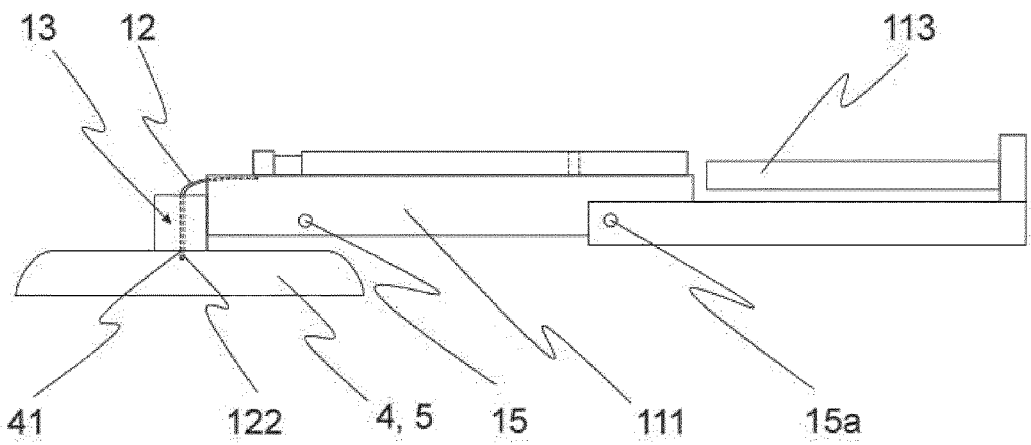

FIG. 2b shows the reservoir assembly 100 according to FIG. 1 with the support unit 111 coupled indirectly to the flexible reservoir 4 (not visible) by the reservoir locking unit 13, the indirect coupling mediated through the rigid housing 5. The plunger 113 is in the plunger retracted position. The transfer cannula 12 has penetrated the flexible reservoir septum 41 with a cannula outlet end 122.

Figure 2C:
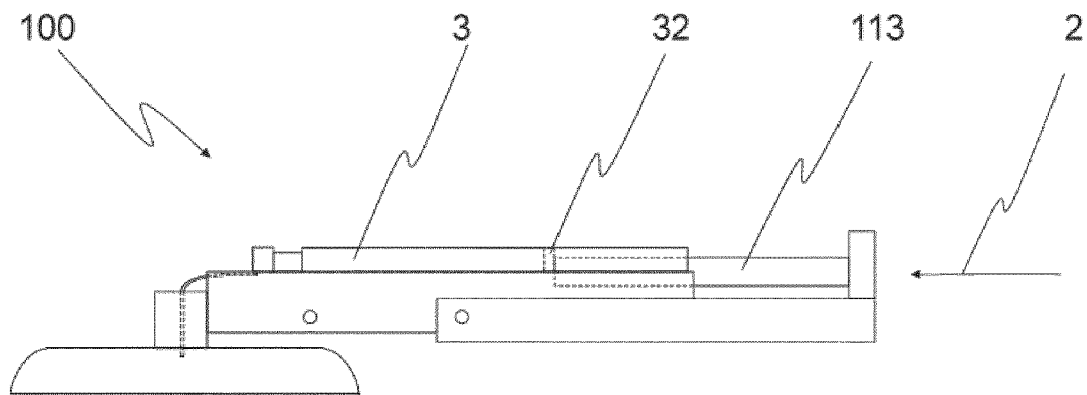

FIG. 2c shows the reservoir assembly 100 according to FIG. 1 during transfilling, in a configuration where the plunger 113 is in a position between the plunger retracted position and a plunger advanced position, pushing the piston 32 of the cartridge 3 from the piston retracted position to a piston advanced position along the advancement direction 2. The part of the plunger 113 being inside the cartridge 3 is indicated by dashed lines.

At some point during the advancement, the front edge 112b of the sliding unit 112 will come in contact with the pins 15. Further advancement of the sliding unit 112 results in the pin 15 elastically forcing the side walls of the sliding unit 112 outwards (perpendicular to the direction of viewing. As the sliding unit 112 is still further advanced. The pins 15 are in sliding contact engagement with the insides of the sidewalls of the sliding unit 112, until the pins 15 finally engage the notches 15a, thereby locking the sliding unit 15) in the plunger advanced position.

A guiding structure (not visible), such as a ramp-shaped sliding surface may be optionally present on the inside of the side walls of the sliding unit 112 and be in sliding contact with the pin 15 in an engaged configuration of the pin 15 and the sliding unit 112.

Figure 2D:
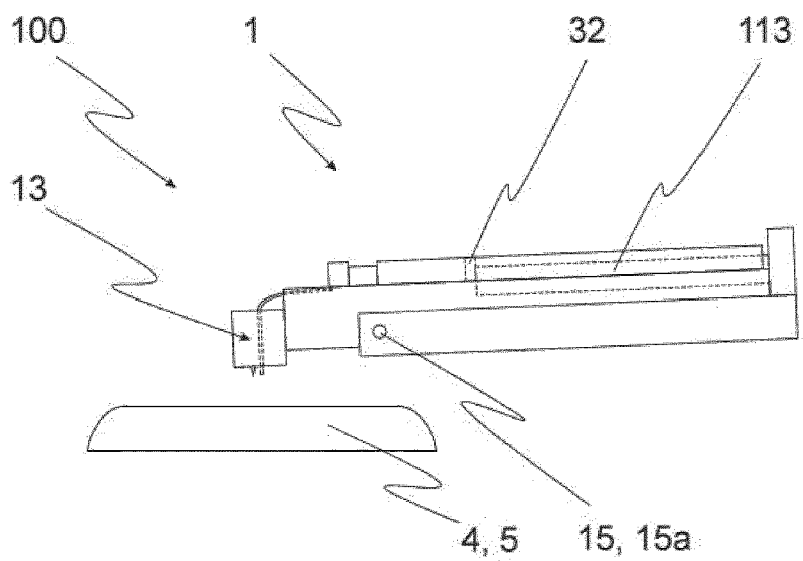

FIG. 2d shows the reservoir assembly 100 according to FIG. 1 after the transfilling, in a configuration where the plunger 113 is in the plunger advanced position and the piston 32 in the piston advanced position. The pins 15 and the notches 15a are shown unreleasably engaged such that the plunger 113 is locked in the plunger advanced position. The coupling of the reservoir locking unit 13 is released, since the plunger 113 has reached the plunger advanced position, and the transfilling device 1 and the rigid housing 5 containing the flexible reservoir 4 can be separated.

FIG. 3 shows another embodiment of the reservoir assembly 100' including another embodiment of a transfilling device 1'. The transfilling device 1' includes another embodiment of a reservoir locking unit 13'. The sliding unit is not shown for clarity reasons. Furthermore, another embodiment of a counter reservoir-locking unit 14' is shown in FIG. 3. The reservoir locking unit 13' and the counter reservoir-locking unit 14' are configured to engage in a sliding fashion along the advancement direction 2. A shoulder 132' on the reservoir locking unit 13' abuts an edge 142' on the counter reservoir-locking unit 14' as the reservoir locking unit 13' is engaged with the counter reservoir-locking unit 14'. An embodiment of a transfer cannula 12' is shown arranged at the reservoir locking unit 13'. The transfer cannula 12' is arranged substantially parallel to the advancement direction 2 such that the transfer cannula 12' does not block the sliding movement of the reservoir locking unit 13' while engaging with the counter reservoir-locking unit 14'.

FIG. 4a, 4b show another embodiment of a plunger locking unit comprising resilient catches 15' and a notch 15a' in a magnified top view of the transfilling device, the notch 15a' being shown by means of a partially cut illustration of the sliding element 112. The catches 15' may unreleasably engage with the notch 15a'. Two configurations of the catches 15' and the notch 15a' before (FIG. 4a) and after (FIG. 4b) engaging are shown on the left and the right of FIG. 4, respectively. The notch 15a' is arranged within a rear wall 112a of the sliding unit 112. The plunger 113 below which the catches 15' are positioned in the shown top view is illustrated by dashed lines. The catches 15' are arranged at or integrally formed with the support unit 111. By moving the support unit 111 and the sliding unit 112 towards each other the catches 15' engage with the notch 15a' such that the support unit 111 and the sliding unit 112 are locked in the shown fixed position (right side of FIG. 4).

Further embodiments of plunger locking units with alternative arrangements of pins, protrusion, catches, notches, or the like may be used as well.

FIG. 5a shows a magnified view of a part of another embodiment of a reservoir assembly 100" comprising another embodiment of a reservoir locking unit 13". Parts of the reservoir assembly 100" shown only partially are delimited by wavy lines. The reservoir locking unit 13" comprises a catch 133 which is pivotably arranged in a pivot 136. The pivot 136 is arranged at the reservoir locking unit 13". Preferably, the catch 133 is resiliently pivotable such that without an external action, the catch 133 always returns back to the shown position after pivoting. The catch 133 comprises protrusions 134 which are configured to be pushed by arms 114 of the sliding element 112' when the sliding element 112' is moved along the advancement direction 2 causing the catch 133 to pivot. The reservoir locking unit 13" is configured to couple to a counter reservoir-locking unit 14" arranged at or integrally formed with a rigid housing 5 containing a flexible reservoir 4. The counter reservoir-locking unit 14" is shown partially cut in the Figure. The counter reservoir-locking unit 14" may be a flange arranged circumferentially around a port 51 of the rigid housing 5 and which may latching engage with the catch 133 of the reservoir locking unit 13". In the shown embodiment, the reservoir locking unit 13" further comprises a ridge 135 which abuts the counter reservoir-locking unit 14". The abutment of the ridge 135 with the counter reservoir-locking unit 14", as shown in the Figure, provides the resistance required for the latching engagement of the counter reservoir-locking unit 14" and the catch 133. In the configuration shown in the Figure, the sliding element 112' is in a configuration where the plunger (not shown) is between the plunger retracted and the plunger advanced position. In the shown embodiment, the plunger locking unit comprises pins 15 and notches 15a.

FIG. 5b shows the reservoir assembly 100" according to FIG. 5a with the sliding element 112' in a configuration where the plunger (not shown) is in the plunger advanced position. The pins 15 and the notches 15a are unreleasably engaged such that the support unit 111 and the sliding unit 112' are locked in the shown fixed position. The configuration shown in FIG. 5b is reached starting from the configuration shown in FIG. 5a by pushing the sliding unit 112' relative to the support unit 111 along the advancement direction 2 which causes the arm 114 of the sliding unit 112' to push the protrusion 134 along the advancement direction 2. By pushing the protrusion 134, the catch 133 pivots around the pivot 136 such that the reservoir locking unit 13" is released from the counter reservoir-locking unit 14" and the transfilling device 1" and the rigid housing 5 are released from each other.

The catch 133 may be a separate element or may be formed integrally with other components of the transfilling device, particularly with the support unit 111. In such embodiments, pivoting of the catch 133 may be achieved via material elasticity. In further embodiments, the contact area between the sliding unit 112, particularly the arm 114, and the catch 133 is located on the other side of the pivot 136 (below the pivot 136 in FIG. 5a, 5b).

In the embodiment of FIG. 5a, 5b, unlocking is achieved via a radial pivoting of the catch 133, perpendicular to the axis as defined by the cannula outlet end 122. In alternative embodiments, the unlocking is achieved via a pivoting relative movement between the transfilling device and the reservoir unit. In such embodiments, the transfilling device and the flexible reservoir 4 and/or the housing 5 may comprise mating bayonet couplers as generally known in the art. A locking unit, particularly a bayonet locking unit, may be provided to lock the transfilling device and the flexible reservoir or the housing encasing the flexible reservoir in the engaged state, e. g. via a locking pin or locking catch and a corresponding cut-out or notch, as generally known in the art. Upon the sliding unit reaching the plunger advanced position, the bayonet locking unit may be released, e.g. via an 13 m 114 similar to the embodiment of FIG. 5a, 5b.

In the before-discussed embodiments, the reservoir locking unit comprises movable elements, particularly the catch 133 for releasing the locking or coupling between the transfilling device and the reservoir, while the counter reservoir locking unit comprises non-movable elements. In alternative similar arrangements, however, the reservoir locking unit comprises non-movable elements, such as non-movable catches and/or protrusions, while the counter reservoir locking unit comprises one or more corresponding movable counter-elements.

The invention claimed is:

1. Transfilling device for transfilling a liquid drug from a cartridge to a flexible reservoir, the transfilling device including:
   a support unit and a plunger, the support unit configured to receive the cartridge, the plunger being insertable into the cartridge, wherein the plunger is displaceable relative to the support unit along an advancement direction between a plunger retracted position, where the plunger is in a most distal position relative to the support unit, and a plunger advanced position, where the plunger is in a most proximal position relative to the support unit, wherein the plunger is configured to push a piston of the cartridge from a piston retracted position to a piston advanced position by displacing the plunger;
   a transfer cannula, wherein the transfer cannula is configured to penetrate a flexible reservoir septum with a cannula outlet end and to penetrate a cartridge septum with a cannula inlet end and thereby to fluidly couple the flexible reservoir with the cartridge;
   a reservoir locking unit, wherein the reservoir locking unit has a coupling configured to releasably mechanically couple the support unit to the flexible reservoir when at least in the plunger retracted position and wherein the coupling of the reservoir locking unit is configured to release the support unit from the flexible reservoir in an automatic manner when in the plunger advanced position; and
   a sliding unit engaged with the support unit in a sliding manner, wherein the sliding unit has the plunger; and
   wherein the sliding unit is configured to engage the coupling of the reservoir locking unit to release the support unit from the flexible reservoir when in the plunger advanced position.

2. Transfilling device according to claim 1, wherein the support unit is designed to receive a cylindrical cartridge having a filling volume between 1 and 4 ml.

3. Transfilling device according to claim 1, wherein the plunger includes a motor coupler, configured to couple to a motor.

4. Transfilling device according to claim 1, wherein the plunger is manually movable.

5. Transfilling device according to claim 1, wherein the plunger is formed integral with the sliding unit.

6. Reservoir assembly including the flexible reservoir and the transfilling device according to claim 1.

7. Reservoir assembly according to claim 6, further including a rigid housing, wherein the flexible reservoir is mounted inside the rigid housing and the rigid housing including at least one port, the rigid housing made of plastic.

8. Reservoir assembly according to claim 7, wherein the rigid housing includes the counter reservoir-locking unit, the counter reservoir-locking unit configured to engage with the reservoir locking unit.

9. Reservoir assembly according to claim 6, wherein the reservoir assembly further includes a counter reservoir-locking unit, the counter reservoir-locking unit configured to engage with the reservoir locking unit.

10. Reservoir assembly according to claim 6, wherein the flexible reservoir has a main extension plane, the main extension plane being substantially parallel to the advancement direction.

11. Reservoir assembly according to claim 6, further including a dosing unit or an interface for mechanical and fluidic coupling to a dosing unit.

12. Infusion system including a dosing unit and the reservoir assembly according to claim 6, wherein the reservoir assembly is fluidly coupled to the dosing unit.

13. Transfilling device for transfilling a liquid drug from a cartridge to a flexible reservoir, the transfilling device including:
  a support unit and a plunger, the support unit configured to receive the cartridge, the plunger being insertable into the cartridge, wherein the plunger is displaceable relative to the support unit along an advancement direction between a plunger retracted position, where the plunger is in a most distal position relative to the support unit, and a plunger advanced position, where the plunger is in a most proximal position relative to the support unit, wherein the plunger is configured to push a piston of the cartridge from a piston retracted position to a piston advanced position by displacing the plunger;
  a transfer cannula, wherein the transfer cannula is configured to penetrate a flexible reservoir septum with a cannula outlet end and to penetrate a cartridge septum with a cannula inlet end and thereby to fluidly couple the flexible reservoir with the cartridge;
  a reservoir locking unit, wherein the reservoir locking unit is configured to releasably mechanically couple the support unit to the flexible reservoir and wherein the coupling of the reservoir locking unit is designed such that the coupling is released in the plunger advanced position; and
  wherein the plunger and the support unit are configured to unreleasably lock in the plunger advanced position.

14. Transfilling device according to claim 13, wherein the plunger includes a motor coupler, configured to couple to a motor.

15. Transfilling device according to claim 13, wherein the plunger is manually movable.

16. Transfilling device according to claim 13, further including a sliding unit, wherein the plunger is formed integral with the sliding unit, the sliding unit being configured for sliding engagement with the support unit.

17. Reservoir assembly including the flexible reservoir and the transfilling device according to claim 13.

18. Reservoir assembly according to claim 17, further including a rigid housing, wherein the flexible reservoir is mounted inside the rigid housing and the rigid housing including at least one port, the rigid housing made of plastic.

19. Reservoir assembly according to claim 17, wherein the reservoir assembly further includes a counter reservoir-locking unit, the counter reservoir-locking unit configured to engage with the reservoir locking unit.

20. Reservoir assembly according to claim 17, further comprising a rigid housing, wherein the rigid housing includes a counter reservoir-locking unit, the counter reservoir-locking unit configured to engage with the reservoir locking unit.

21. Reservoir assembly according to claim 17, wherein the flexible reservoir has a main extension plane, the main extension plane being substantially parallel to the advancement direction.

22. Reservoir assembly according to claim 17, further including a dosing unit or an interface for mechanical and fluidic coupling to a dosing unit.

23. Infusion system including a dosing unit and the reservoir assembly according to claim 17, wherein the reservoir assembly is fluidly coupled to the dosing unit.

24. Method for transfilling a liquid drug from a cartridge to a flexible reservoir the method including:
  providing a transfilling device;
  releasably coupling a support unit of the transfilling device to the flexible reservoir by a coupling of a reservoir locking unit;
  receiving the cartridge in the support unit;
  fluidly coupling the cartridge to the flexible reservoir by a transfer cannula, the transfer cannula penetrating a flexible reservoir septum with a cannula outlet end and penetrating a cartridge septum with a cannula inlet end;
  displacing a plunger relative to the support unit along an advancement direction from a plunger retracted position, where the plunger is in a most distal position relative to the support unit to a plunger advanced position, where the plunger is in a most proximal position relative to the support unit;
  wherein said displacing the plunger includes pushing a piston of the cartridge from a piston retracted position to a piston advanced position, thereby transfilling the liquid drug from the cartridge to the flexible reservoir;
  releasing in an automatic manner the support unit from the flexible reservoir when in the plunger advanced position;
  wherein the coupling is a mechanical coupling;
  wherein the support unit is slidingly coupled to a sliding unit with the plunger; and
  wherein said releasing includes engaging the sliding unit with the mechanical coupling of the reservoir locking unit when in the plunger advanced position.

25. Method for transfilling a liquid drug from a cartridge to a flexible reservoir using a transfilling device, wherein the transfilling device includes:
  a support unit and a plunger, the support unit configured to receive the cartridge, the plunger being insertable into the cartridge, wherein the plunger is displaceable relative to the support unit along an advancement direction between a plunger retracted position, where the plunger is in a most distal position relative to the support unit, and a plunger advanced position, where the plunger is in a most proximal position relative to the support unit, wherein the plunger is configured to push a piston of the cartridge from a piston retracted position to a piston advanced position by displacing the plunger;
  a transfer cannula, wherein the transfer cannula is configured to penetrate a flexible reservoir septum with a cannula outlet end and to penetrate a cartridge septum with a cannula inlet end and thereby to fluidly couple the flexible reservoir with the cartridge;
  a reservoir locking unit, wherein the reservoir locking unit has coupling configured to releasably mechanically couple the support unit to the flexible reservoir when at least in the plunger retracted position and wherein the coupling of the reservoir locking unit is configured to release the support unit from the flexible reservoir in an automatic manner when in the plunger advanced position; and
  a sliding unit engaged with the support unit in a sliding manner, wherein the sliding unit has the plunger; and
  wherein the sliding unit is configured to engage the coupling of the reservoir locking unit to release the support unit form the flexible reservoir when in the plunger advanced position.

26. The method of claim 15, further comprising:
  using a reservoir assembly that includes the flexible reservoir and the transfilling device.

* * * * *